United States Patent
Tsai et al.

(10) Patent No.: US 9,770,276 B2
(45) Date of Patent: Sep. 26, 2017

(54) BIONIC FIXING APPARATUS

(71) Applicants: INDUSTRIAL TECHNOLOGY RESEARCH INSTITUTE, Hsinchu (TW); NATIONAL TAIWAN UNIVERSITY HOSPITAL, Taipei (TW)

(72) Inventors: Pei-Yi Tsai, Hsinchu (TW); Chih-Chieh Huang, Zhunan Township (TW); Yi-Hung Wen, Hsinchu (TW); Hsin-Hsin Shen, Zhudong Township (TW); Yi-Hung Lin, Zhubei (TW); De-Yau Lin, Tainan (TW); Jui-Sheng Sun, Taipei (TW); Chuan-Sheng Chuang, Taichung (TW); An-Li Chen, Tainan (TW); Ching-Chih Lin, Kaohsiung (TW)

(73) Assignees: INDUSTRIAL TECHNOLOGY RESEARCH INSTITUTE, Hsinchu (TW); NATIONAL TAIWAN UNIVERSITY HOSPITAL, Taipei (TW)

( * ) Notice: Subject to any disclaimer, the term of this patent is extended or adjusted under 35 U.S.C. 154(b) by 197 days.

(21) Appl. No.: 14/555,204

(22) Filed: Nov. 26, 2014

(65) Prior Publication Data

US 2015/0147722 A1 May 28, 2015

Related U.S. Application Data

(60) Provisional application No. 61/908,772, filed on Nov. 26, 2013.

(30) Foreign Application Priority Data

May 30, 2014 (TW) .............................. 103118970 A (51) Int. Cl.
A61C 8/00 (2006.01)
A61B 17/86 (2006.01)
(Continued)

(52) U.S. Cl.
CPC .......... *A61B 17/8625* (2013.01); *A61B 17/72* (2013.01); *A61C 8/0018* (2013.01);
(Continued)

(58) Field of Classification Search
CPC ................ A61B 17/72; A61B 17/8625; A61C 2008/0046; A61C 8/0018; A61C 8/0022; A61C 8/0037; A61F 2/442
See application file for complete search history.

(56) References Cited

U.S. PATENT DOCUMENTS 5,370,695 A 12/1994 Meuli et al.
5,876,434 A * 3/1999 Flomenblit .......... A61C 8/0033
433/172
(Continued)

FOREIGN PATENT DOCUMENTS

CN 1088423 A 6/1994
CN 1098281 A 2/1995
(Continued)

OTHER PUBLICATIONS

Taiwanese Office Action and Search Report for Taiwanese Application No. 103118970, dated Feb. 15, 2016.
(Continued)

*Primary Examiner* — Lindsey G Wehrheim
(74) *Attorney, Agent, or Firm* — Birch, Stewart, Kolasch & Birch, LLP (57) ABSTRACT

A bionic fixing apparatus is provided. The bionic fixing apparatus includes a flexible portion having at least one trench. The trench is disposed on the surface of the flexible portion and has a first end and a second end. An interval is
(Continued)

disposed between the first end and the second end. The trench is disposed for spreading the stress applied on the bionic fixing apparatus and preventing stress concentration and stress shielding.

13 Claims, 7 Drawing Sheets

(51) Int. Cl.
  A61B 17/72 (2006.01)
  A61F 2/44 (2006.01)
(52) U.S. Cl.
  CPC .......... *A61C 8/0022* (2013.01); *A61C 8/0037* (2013.01); *A61C 2008/0046* (2013.01); *A61F 2/442* (2013.01)

(56) References Cited

U.S. PATENT DOCUMENTS

| | | | |
|---|---|---|---|
| 8,388,660 | B1 | 3/2013 | Abdou |
| 2004/0210217 | A1 | 10/2004 | Baynham et al. |
| 2005/0112397 | A1 | 5/2005 | Rolfe et al. |
| 2005/0143823 | A1* | 6/2005 | Boyd ............... A61B 17/7032 623/17.16 |
| 2005/0192675 | A1 | 9/2005 | Robinson |
| 2006/0100630 | A1 | 5/2006 | West, Jr. |
| 2006/0106390 | A1 | 5/2006 | Jensen et al. |
| 2007/0265622 | A1 | 11/2007 | Aeschlimann et al. |
| 2009/0240289 | A1 | 9/2009 | Zipprich et al. |
| 2010/0042215 | A1 | 2/2010 | Stalcup et al. |
| 2011/0123951 | A1 | 5/2011 | Lomicka |
| 2011/0166602 | A1 | 7/2011 | Malek |
| 2011/0213423 | A1 | 9/2011 | Biedermann et al. |
| 2011/0307073 | A1 | 12/2011 | Teoh et al. |
| 2012/0271362 | A1 | 10/2012 | Martineau et al. |
| 2015/0093717 | A1 | 4/2015 | Ali |

FOREIGN PATENT DOCUMENTS

| | | |
|---|---|---|
| CN | 1204498 A | 1/1999 |
| CN | 1604759 A | 4/2005 |
| CN | 1891172 A | 1/2007 |
| CN | 2894638 Y | 5/2007 |
| CN | 101198291 A | 6/2008 |
| CN | 201082188 Y | 7/2008 |
| CN | 101317790 A | 12/2008 |
| CN | WO 201840550 U | 5/2011 |
| CN | 202682036 U | 1/2013 |
| CN | 202821579 U | 3/2013 |
| CN | 103167837 A | 6/2013 |
| EP | 1 112 722 A2 | 7/2001 |
| EP | 1 069 872 B1 | 5/2003 |
| EP | 1 762 189 A1 | 3/2007 |
| EP | 2400901 B1 | 5/2013 |
| TW | 330839 | 5/1998 |
| TW | 480169 B | 3/2002 |
| TW | 200416020 A | 9/2004 |
| TW | 200635565 A | 10/2006 |
| TW | 200708295 A | 3/2007 |
| TW | 200722036 A | 6/2007 |
| TW | I306396 B | 2/2009 |
| TW | 200936113 A | 9/2009 |
| TW | 200944176 A1 | 11/2009 |
| TW | 201100061 A | 1/2011 |
| TW | 201221108 A1 | 6/2012 |
| TW | 201235005 A1 | 9/2012 |
| TW | 201240653 A | 10/2012 |
| TW | 201249392 A | 12/2012 |
| TW | 201325577 A1 | 7/2013 |
| TW | 201325638 A1 | 7/2013 |
| TW | M458938 U | 8/2013 |
| WO | WO 2011/059995 A2 | 5/2011 |
| WO | WO 2012/024665 A2 | 2/2012 |
| WO | WO 2013/043218 A1 | 3/2013 |
| WO | WO 2013/043432 A1 | 3/2013 |

OTHER PUBLICATIONS

Taiwanese Office Action and Search Report for Taiwanese Application No. 103122519, dated Dec. 2, 2015.
Taiwanese Office Action and Search Report for Taiwanese Application No. 103122817, dated Nov. 26, 2015.
"Setting the Stage for What is Next", 2012 United States Medical Devices Outlook, NB3E-54, Jul. 2012.
Achour et al., "Stress distribution in dental implant with elastomeric stress barrier", Materials and Design, 2011, vol. 32, pp. 282-290.
Breguet et al., "Compact, Light Weight Mechanisms for High Precision Micro-Manipulators", pp. 1-5.
Chen et al., "Pullout strength for cannulated pedicle screws with bone cement augmentation in severely osteoporotic bone: Influences of radial hole and pilot hole tapping", Clinical Biomechanics, 2009, vol. 24, pp. 613-618.
Emmelmann et al, "Laser freeform fabrication of porous network structures for dental application", Proceedings of the Fifth International WLT-Conference on Lasers in Manufacturing 2009, Munich, Jun. 2009, pp. 453-457.
Kissel et al., "Comparison of Pullout Strength of Small-Diameter Cannulated and Solid-Core Screws", The Journal of Foot & Ankle Surgery, Nov./Dec. 2003, vol. 42, No. 6, pp. 334-338.
Lin et al., "A biomechanical study of the cortex-anchorage vertebral screw", Clinical Biomechanics, 2003, vol. 18, pp. S25-S32.
Liu et al., "Design and biomechanical study of a modified pedicle screw", Chinese Journal of Traumatology, 2010, vol. 13, No. 4, pp. 222-228.
Migliorati et al., "Miniscrew design and bone characteristics: An experimental study of primary stability"; AJO-DO, Aug. 2012, vol. 142, No. 2, pp. 228-234.
Mikos et al., "Laminated three-dimensional biodegradable foams for use in tissue engineeing", Biomaterials, 1993, vol. 14, No. 5, pp. 323-330.
Richman, MD, "Odontoid Screw Fixation for Type II Odontoid Fractures", Operative Techniques in Orthopaedics, Jan. 1998, vol. 8, No. 1, pp. 16-21.
Shen et al., "Hollow-Bone-Graft Dynamic Hip Screw Can Fix and Promote Bone Union after Femoral Neck Fracture: an Experimental Research", International Journal of Medical Sciences, 2012, vol. 9, No. 10, pp. 916-922: doi:10.7150/ijms.4567.
Sumner et al., "Functional adaptation and ingrowth of bone vary as a function of hip implant stiffness", Journal of Biomechanics, 1998, vol. 31, pp. 909-917.
Chinese Office Action and Search Report for Chinese Application No. 201410406040.6, dated Jan. 17, 2017.
Taiwanese Office Action and Search Report for Taiwanese Application No. 104140981, dated Feb. 18, 2017.

* cited by examiner

BIONIC FIXING APPARATUS

CROSS-REFERENCE TO RELATED APPLICATION

This application claims the benefits of U.S. provisional application 61/908,772, filed Nov. 26, 2013, and Taiwan application Serial No. 103118970, filed May 30, 2014, the disclosures of which are incorporated by reference herein in its entirety.

TECHNICAL FIELD

The technical field relates to to a bionic fixing apparatus.

BACKGROUND

With the advances in technology and medicine, implants, such as bone screws, are used to fix the biological tissue in the human body for medical purpose, for example, for repairing accidental injury or nature aging.

However, modulus of elasticity of the conventional implants (which is about 100 Gpa) is much higher than that of the biological tissue in human body (which is lower than 1 Gpa). When the force applied is too high, the tissue tends to, necrosis, wear, and the implants may also be loosened. In general, the conventional process of manufacturing implants includes a special sintering process or a surface coating process to the implants, and then executing a surface treatment by laser to enhance bone integration. But the conventional process has limitation for improving the stress shielding effect of the implants. And the small size of implants may also increase the difficulty in a traditional process.

SUMMARY

The disclosure is directed to a bionic fixing apparatus having a flexible portion. At least one trench is formed on the surface of the implants by additive manufacturing process, and the trench structure may effectively decrease modulus of elasticity of the implants to prevent the tissue from sagging, necrosis, wearing, or to prevent the implants from loosening.

According to one embodiment, a bionic fixing apparatus is provided. The bionic fixing apparatus includes a flexible portion having at least one trench. The trench is disposed on the surface of the flexible portion and has a first end and a second end. An interval is disposed between the first end and the second end. The trench is disposed for spreading the stress applied on the bionic fixing apparatus and preventing stress concentration and stress shielding.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The bionic fixing apparatus according to the embodiment of the disclosure includes a flexible portion having at least one trench. The trench is disposed on the surface of the flexible portion and has a first end and a second end. An interval is disposed between the first end and the second end. That is, the first end and the second end disconnect to each other, and the trench is not formed as an enclosed region. In the embodiment, the trench is disposed for spreading the stress applied on the bionic fixing apparatus.

The following first to seventh embodiments are described with reference to the FIG. 1A to FIG. 7, and are took as examples to illustrate the bionic fixing apparatus of the disclosure. In these embodiments, the bionic fixing apparatus is shown by a schematic perspective view or the track of the trench of the bionic fixing apparatus in different planes.

First Embodiment

Figure 1A:
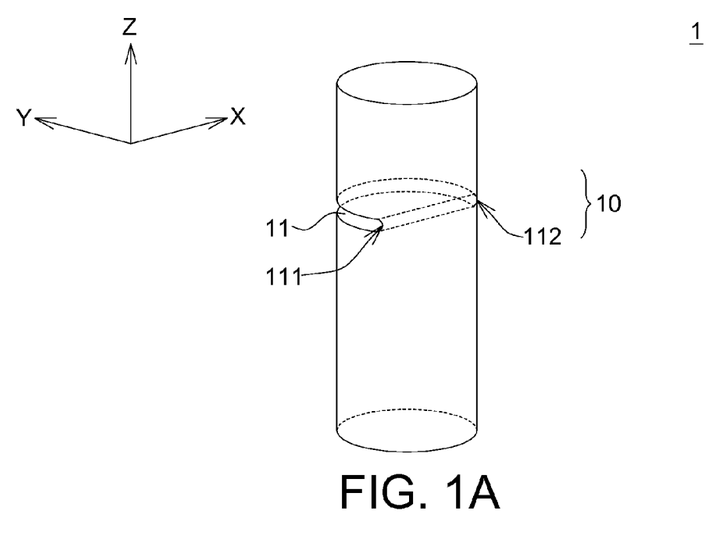
FIG. 1A illustrates a bionic fixing apparatus according to the first embodiment of the disclosure.

FIG. 1A illustrates a bionic fixing apparatus 1 according to the first embodiment of the disclosure. The bionic fixing apparatus 1 includes a flexible portion 10 having a trench 11, and the trench 11 is disposed on the surface of the flexible portion 10. The trench 11 has a first end 111 and a second end 112, and an interval is disposed between the first end 111 and the second end 112. That is, the first end 111 and the second end 112 disconnect to each other, and the trench 11 is not formed as an enclosed region.

Figure 1B:
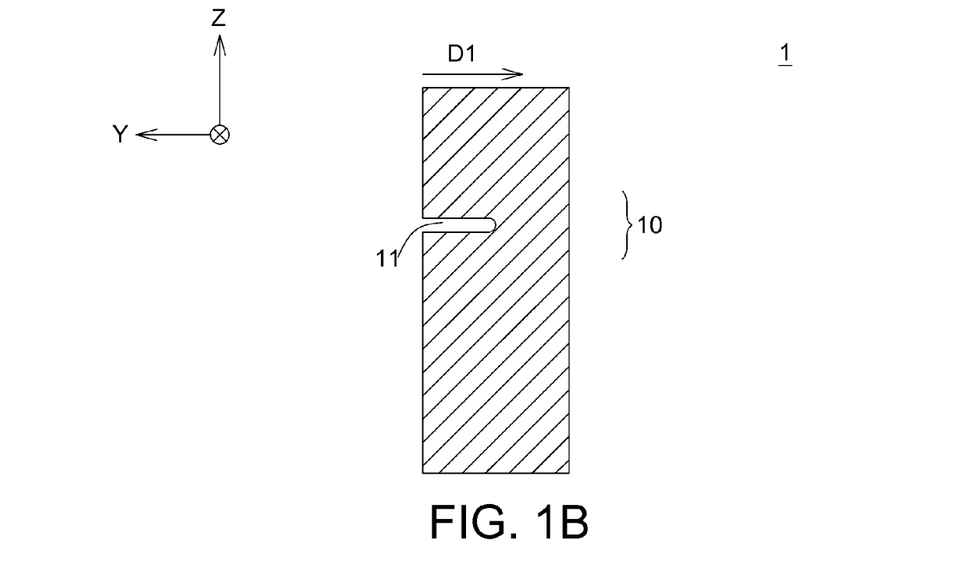
FIG. 1B illustrates a side view of the bionic fixing apparatus (in Y-Z plane) according to the first embodiment of the disclosure.

FIG. 1B illustrates a side view of the bionic fixing apparatus 1 (in Y-Z plane) according to the first embodiment of the disclosure. As shown in FIG. 1B, the trench 11 of the bionic fixing apparatus 1 according to the first embodiment of the disclosure is disposed along a first direction D1 in Y-Z plane and extended on the surface of the flexible portion 10. In this embodiment, the first direction D1 is perpendicular to a force-receiving direction of the bionic fixing apparatus 1.

In one embodiment, the force-receiving direction of the bionic fixing apparatus 1 is, for example, parallel with Z-direction.

FIG. 10 illustrates the trench 11 of the bionic fixing apparatus 1 (in X-Y plane) according to the first embodiment of the disclosure. FIG. 10 illustrates the structure of the trench 11 of the bionic fixing apparatus 1 from another point of view (another plane). In this embodiment, the trench 11 is disposed along a track in a first plane (X-Y plane), and extended on the surface of the flexible portion 10. Here, the first plane is perpendicular to the force-receiving direction (Z-direction) of the bionic fixing apparatus 1. For example, the trench 11 is disposed along track T1 in X-Y plane, and extended on the surface of the flexible portion 10 as shown in FIG. 1C.

In the embodiments of the disclosure, the track is an arc line with radian less than $2\pi$. For, example, track T1 shown in FIG. 1C is an arc line along radian 0 to $\pi$. However, the disclosure is not limited thereto. In other embodiments, the track may be an arc line along other radians.

Figure 1C:
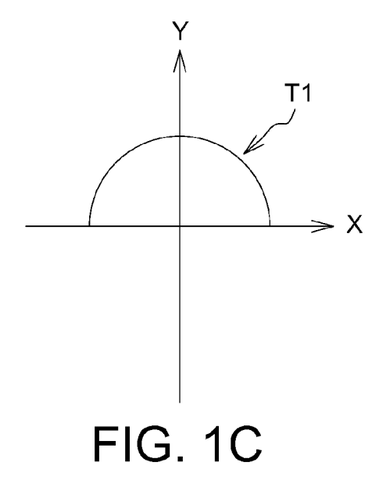
FIG. 1C illustrates the trench of the bionic fixing apparatus (in X-Y plane) according to the first embodiment of the disclosure.
Figure 1D:
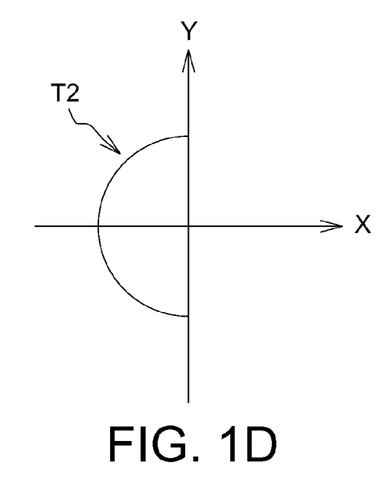
FIG. 1D to FIG. 1F illustrate the trench of the bionic fixing apparatus (in X-Y plane) according to other embodiments of the disclosure.
Figure 1E:
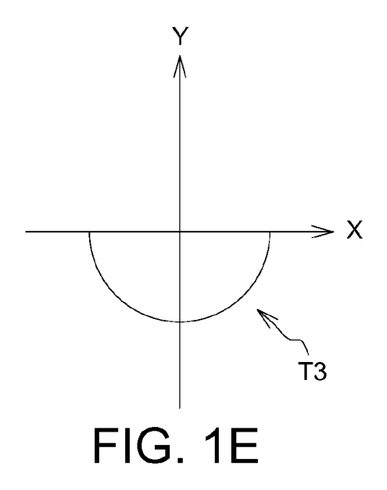
Figure 1F:
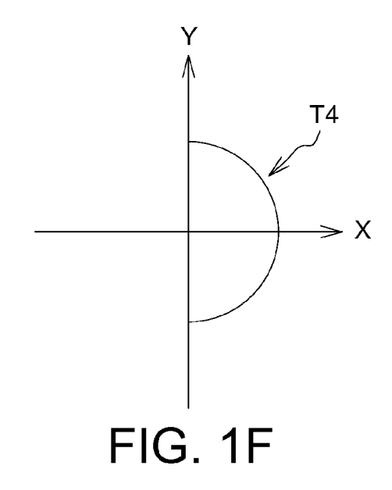

FIG. 1D to FIG. 1F illustrate the trench 11 of the bionic fixing apparatus 1 (in X-Y plane) according to other embodiments of the disclosure. In FIG. 1D, track T2 is such as an arc line along radian $\pi/2$ to $3\pi/2$; in FIG. 1E, track T3 is such as an arc line along radian $\pi$ to $2\pi$; in FIG. 1F, track T4 is such as an arc line along radian $-\pi/2$ to $\pi/2$.

It should be noted that although track T1 shown in FIG. 1C, track T2 shown in FIG. 1D, track T3 shown in FIG. 1E and track T4 shown in FIG. 1F are all arc lines with radian equal to $\pi$, the disclosure is not limited thereto. In fact, the track according to the embodiment of the disclosure is an arc line with radian less than $2\pi$. That is, a trench having a first end 111 and a second end 112 disconnected to each other may be the trench 11 according to the embodiment of the disclosure.

The above-mentioned trench 11 observed in the first plane (X-Y plane) and the second plane (Y-Z plane) is shown by simplifying the bionic fixing apparatus according to the first embodiment of the disclosure to have a cylindrical, cone or similar shapes. That is, the trench 11 may be disposed substantially along the circumferential direction of the cylinder or cone, and extended on the surface of the flexible portion 10.

Since the bionic fixing apparatus 1 according to the first embodiment of the disclosure includes the trench 11, a small space formed by the trench may be used as a buffer when the bionic fixing apparatus 1 is subjected to an external force. For example, assumed that a 100 N external force parallel with Z-direction is applied to the bionic fixing apparatus 1, the bionic fixing apparatus 1 may generate a displacement of approximately $4.998 \times 10^{-2}$ mm. The displacement may be used as a buffer when the bionic fixing apparatus 1 is subjected to an external force, which prevents stress concentration and stress shielding, such that modulus of elasticity of the bionic fixing apparatus 1 may be decreased effectively to prevent the bionic fixing apparatus 1 from loosening or to prevent the tissue of organisms from sagging, necrosis, wearing.

Second Embodiment

Figure 2A:
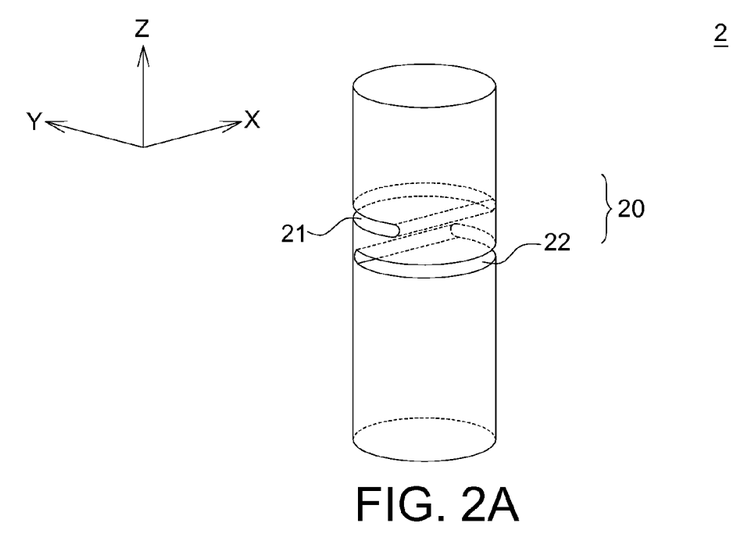
FIG. 2A illustrates a bionic fixing apparatus according to the second embodiment of the disclosure.

FIG. 2A illustrates a bionic fixing apparatus 2 according to the second embodiment of the disclosure. It is similar to the first embodiment that the bionic fixing apparatus 2 includes a flexible portion 20. The difference between the first embodiment and the second embodiment is that the bionic fixing apparatus 2 includes a first trench 21 and a second trench 22. The first trench 21 and the second trench 22 are disposed on the surface of the flexible portion 20 and have a first end and a second end (not shown). Similarly, an interval is disposed between the first end and the second end of the first trench 21 and the second trench 22 respectively. That is, the first end and the second end disconnect to each other, and the first trench 21 and the second trench 22 are both not formed as an enclosed region.

Figure 2B:
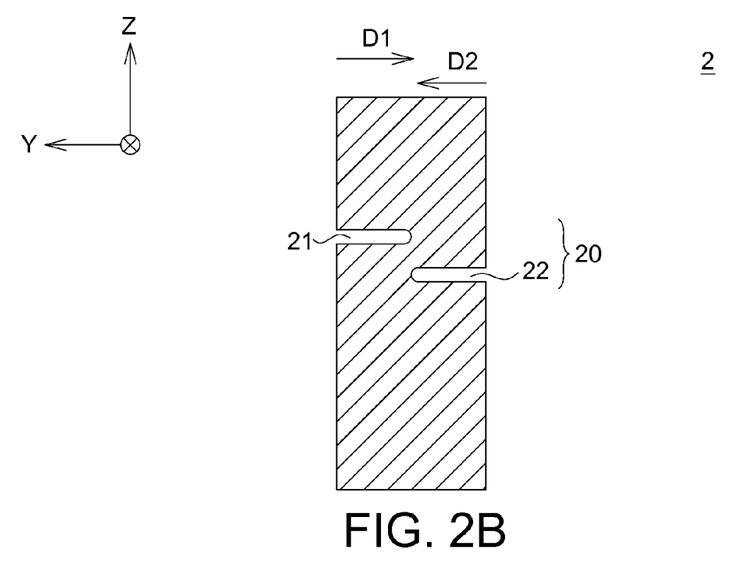
FIG. 2B illustrates a side view of the bionic fixing apparatus (in Y-Z plane) according to the second embodiment of the disclosure.

FIG. 2B illustrates a side view of the bionic fixing apparatus 2 (in Y-Z plane) according to the second embodiment of the disclosure. As shown in FIG. 2B, the first trench 21 of the bionic fixing apparatus 2 according to the second embodiment of the disclosure is disposed along a first direction D1 in Y-Z plane and extended on the surface of the flexible portion 20. The second trench 22 of the bionic fixing apparatus 2 according to the second embodiment of the disclosure is disposed along a second direction D2 in Y-Z plane and extended on the surface of the flexible portion 20. In this embodiment, the first direction D1 and the second direction D2 are perpendicular to a force-receiving direction of the bionic fixing apparatus 2 (and the force-receiving direction of the bionic fixing apparatus 2 is, for example, parallel with Z-direction), and the second direction D2 is opposite to the first direction D1.

The following is an observation of the structure of the first trench 21 and the second trench 22 of the bionic fixing apparatus 2 from another point of view (another plane). In this embodiment, the first trench 21 of the bionic fixing apparatus 2 is disposed along track T1 in X-Y plane as shown in FIG. 1C, and extended on the surface of the flexible portion 20. That is, the first trench 21 is disposed along an arc line along radian 0 to $\pi$, and extended on the surface of the flexible portion 20. The second trench 22 of the bionic fixing apparatus 2 is disposed along track T3 in X-Y plane as shown in FIG. 1E, and extended on the surface of the flexible portion 20. That is, the second trench 22 is disposed along an arc line along radian $\pi$ to $2\pi$, and extended on the surface of the flexible portion 20.

It is not limited that the first trench 21 and the second trench 22 according to the second embodiment of the disclosure are both arc lines with radian equal to $\pi$. In fact, the track according to the embodiment of the disclosure is an arc line with radian less than $2\pi$. That is, a trench having a first end and a second end disconnected to each other may be the first trench 21 and the second trench 22 according to the embodiment of the disclosure.

In this embodiment, assumed that a 100 N external force parallel with Z-direction is applied to the bionic fixing apparatus 2, the bionic fixing apparatus 2 may generate a displacement of approximately $3.647 \times 10^{-2}$ mm. Assumed that a 137 N external force parallel with Z-direction is applied to the bionic fixing apparatus 2, the bionic fixing apparatus 2 may generate a displacement of approximately $4.996 \times 10^{-2}$ mm. Similarly, the displacement may be used as a buffer when the bionic fixing apparatus 2 is subjected to an external force, such that modulus of elasticity of the bionic fixing apparatus 2 may be decreased effectively.

Third Embodiment

Figure 3A:
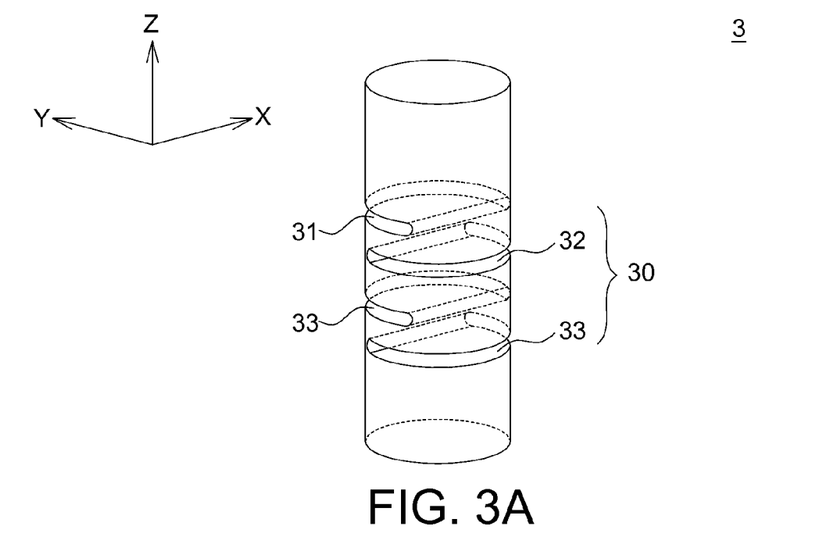
FIG. 3A illustrates a bionic fixing apparatus according to the third embodiment of the disclosure.

FIG. 3A illustrates a bionic fixing apparatus 3 according to the third embodiment of the disclosure. It is similar to the second embodiment that the bionic fixing apparatus 3 includes a flexible portion 30. The difference between the third embodiment and the second embodiment is that the bionic fixing apparatus 3 includes a first trench 31 and a second trench 32, and further includes a third trench 33 and a fourth trench 34. The first trench 31, the second trench 32, the third trench 33 and the fourth trench 34 are disposed on the surface of the flexible portion 30.

Figure 3B:
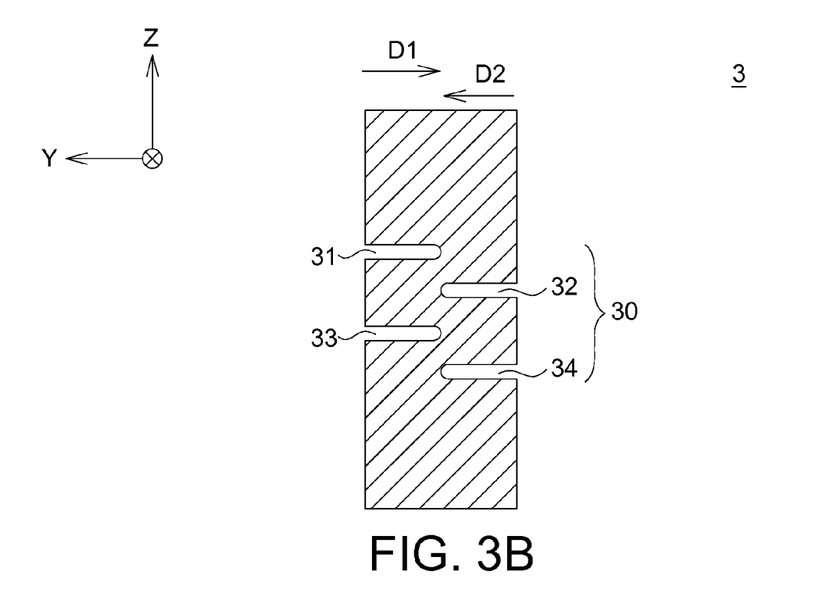
FIG. 3B illustrates a side view of the bionic fixing apparatus (in Y-Z plane) according to the third embodiment of the disclosure.

FIG. 3B illustrates a side view of the bionic fixing apparatus 3 (in Y-Z plane) according to the third embodiment of the disclosure. The first trench 31 and the third trench 33 according to the third embodiment of the disclosure are similar to the first trench 21 according to the second embodiment of the disclosure; the second trench 32 and the fourth trench 34 according to the third embodiment of the disclosure are similar to the second trench 22 according to the second embodiment of the disclosure. In addition, the first trench 31, the second trench 32, the third trench 33 and the fourth trench 34 are formed on the surface of the flexible portion 30 in sequence from top to bottom of the bionic fixing apparatus 3 as shown in FIGS. 3A and 3B. However, the disclosure is not limited thereto. The order of the first trench 31, the second trench 32, the third trench 33 and the fourth trench 34 formed on the surface of the flexible portion 30 may be different from that as shown in FIGS. 3A and 3B.

As shown in FIG. 3B, the first trench 31 and the third trench 33 of the bionic fixing apparatus 3 according to the third embodiment of the disclosure are disposed along a first direction D1 in Y-Z plane and extended on the surface of the flexible portion 30. The second trench 32 and the fourth trench 34 of the bionic fixing apparatus 3 according to the third embodiment of the disclosure are disposed along a second direction D2 in Y-Z plane and extended on the surface of the flexible portion 30. In this embodiment, the first direction D1 and the second direction D2 are perpendicular to a force-receiving direction of the bionic fixing apparatus 3 (and the force-receiving direction of the bionic fixing apparatus 3 is, for example, parallel with Z-direction), and the second direction D2 is opposite to the first direction D1.

The following is an observation of the structure of the first trench 31, the second trench 32, the third trench 33 and the fourth trench 34 of the bionic fixing apparatus 3 from another point of view (another plane). In this embodiment, the first trench 31 and the third trench 33 of the bionic fixing apparatus 3 are disposed along track T1 in X-Y plane as shown in FIG. 1C, and extended on the surface of the flexible portion 30. That is, the first trench 31 and the third trench 33 are disposed along an arc line along radian 0 to $\pi$, and extended on the surface of the flexible portion 30. The second trench 32 and the fourth trench 34 of the bionic fixing apparatus 3 are disposed along track T3 in X-Y plane as shown in FIG. 1E, and extended on the surface of the flexible portion 30. That is, the second trench 32 and the fourth trench 34 are disposed along an arc line along radian $\pi$ to $2\pi$, and extended on the surface of the flexible portion 30.

It is not limited that the first trench 31, the second trench 32, the third trench 33 and the fourth trench 34 according to the third embodiment of the disclosure are all arc lines with radian equal to $\pi$. In fact, the track according to the embodiment of the disclosure is an arc line with radian less than $2\pi$. That is, a trench having a first end and a second end disconnected to each other may be the first trench 31, the second trench 32, the third trench 33 and the fourth trench 34 according to the embodiment of the disclosure.

In this embodiment, assumed that a 100 N external force parallel with Z-direction is applied to the bionic fixing apparatus 3, the bionic fixing apparatus 3 may generate a displacement of approximately $7.731 \times 10^{-2}$ mm. The displacement may be used as a buffer when the bionic fixing apparatus 3 is subjected to an external force, such that modulus of elasticity of the bionic fixing apparatus 3 may be decreased effectively.

Fourth Embodiment

Figure 4A:
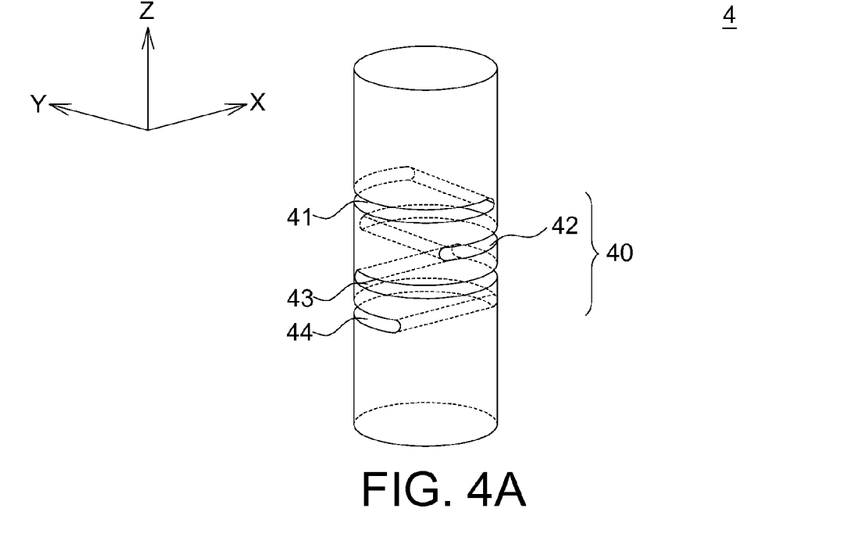
FIG. 4A illustrates a bionic fixing apparatus according to the fourth embodiment of the disclosure.

FIG. 4A illustrates a bionic fixing apparatus 4 according to the fourth embodiment of the disclosure. The bionic fixing apparatus 4 includes a flexible portion 40. The flexible portion 40 includes a first trench 41 and a second trench 42, a third trench 43 and a fourth trench 44 disposed on the surface of the flexible portion 40.

Figure 4B:
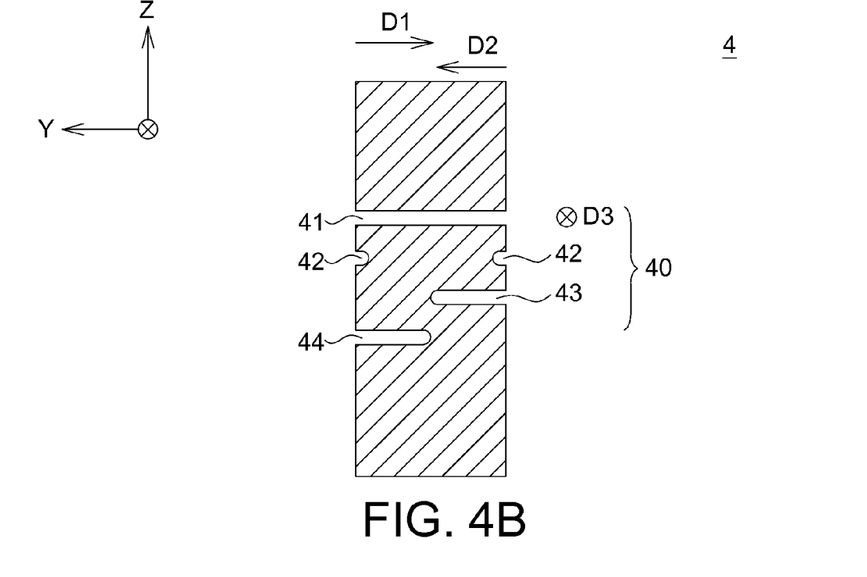
FIG. 4B illustrates a side view of the bionic fixing apparatus (in Y-Z plane) according to the fourth embodiment of the disclosure.

FIG. 4B illustrates a side view of the bionic fixing apparatus 4 (in Y-Z plane) according to the fourth embodiment of the disclosure. The third trench 43 according to the fourth embodiment of the disclosure is similar to the second trench 32 according to the third embodiment of the disclosure; the fourth trench 44 according to the fourth embodiment of the disclosure is similar to the first trench 31 according to the third embodiment of the disclosure. In addition, the first trench 41, the second trench 42, the third trench 43 and the fourth trench 44 are formed on the surface of the flexible portion 40 in sequence from top to bottom of the bionic fixing apparatus 4 as shown in FIGS. 4A and 4B. However, the disclosure is not limited thereto. The order of the first trench 41, the second trench 42, the third trench 43 and the fourth trench 44 formed on the surface of the flexible portion 40 may be different from that as shown in FIGS. 4A and 4B.

As shown in FIG. 4B, the first trench 41 of the bionic fixing apparatus 4 according to the fourth embodiment of the disclosure is disposed along a first direction D1 or a second direction D2 in Y-Z plane, and extended on the surface of the flexible portion 40. The second trench 42 of the bionic fixing apparatus 4 according to the fourth embodiment of the disclosure is disposed along a third direction D3 in Y-Z plane, and extended on the surface of the flexible portion 40. The third trench 43 of the bionic fixing apparatus 4 according to the fourth embodiment of the disclosure is disposed along the second direction D2 in Y-Z plane, and extended on the surface of the flexible portion 40. The fourth trench 44 of the bionic fixing apparatus 4 according to the fourth embodiment of the disclosure is disposed along the first direction D1 in Y-Z plane, and extended on the surface of the flexible portion 40. In this embodiment, the first direction D1, the second direction D2, and the third direction D3 are perpendicular to a force-receiving direction of the bionic fixing apparatus 4 (and the force-receiving direction of the bionic fixing apparatus 4 is, for example, parallel with Z-direction), the second direction D2 is opposite to the first direction D1, and the third direction D3 is perpendicular to the first direction D1 and the second direction D2.

The following is an observation of the structure of the first trench 41, the second trench 42, the third trench 43 and the fourth trench 44 of the bionic fixing apparatus 4 from another point of view (another plane). In this embodiment, the first trench 41 of the bionic fixing apparatus 4 is disposed along track T2 in X-Y plane as shown in FIG. 1D, and extended on the surface of the flexible portion 40. That is, the first trench 41 is disposed along an arc line along radian $\pi/2$ to $3\pi/2$, and extended on the surface of the flexible portion 40. The second trench 42 of the bionic fixing apparatus 4 is disposed along track T4 in X-Y plane as shown in FIG. 1F, and extended on the surface of the flexible portion 40. That is, the second trench 42 is disposed along an arc line along radian $-\pi/2$ to $\pi/2$, and extended on the surface of the flexible portion 40. The third trench 43 of the bionic fixing apparatus 4 is disposed along track T3 in X-Y plane as shown in FIG. 1E, and extended on the surface of the flexible portion 40. That is, the third trench 43 is disposed along an arc line along radian $\pi$ to $2\pi$, and extended on the surface of the flexible portion 40. The fourth trench 44 of the bionic fixing apparatus 4 is disposed along track T1 in X-Y plane as shown in FIG. 10, and extended on the surface of the flexible portion 40. That is, the fourth trench 44 is disposed along an arc line along radian 0 to $\pi$, and extended on the surface of the flexible portion 40.

It is not limited that the first trench 41, the second trench 42, the third trench 43 and the fourth trench 44 according to the fourth embodiment of the disclosure are all arc lines with radian equal to $\pi$. In fact, the track according to the embodiment of the disclosure is an arc line with radian less than $2\pi$. That is, a trench having a first end and a second end disconnected to each other may be the first trench 41, the second trench 42, the third trench 43 and the fourth trench 44 according to the embodiment of the disclosure.

In this embodiment, assumed that a 100 N external force parallel with Z-direction is applied to the bionic fixing apparatus 4, the bionic fixing apparatus 4 may generate a displacement of approximately $9.533 \times 10^{-2}$ mm. The displacement may be used as a buffer when the bionic fixing apparatus 4 is subjected to an external force, such that modulus of elasticity of the bionic fixing apparatus 4 may be decreased effectively.

Fifth Embodiment

Figure 5A:
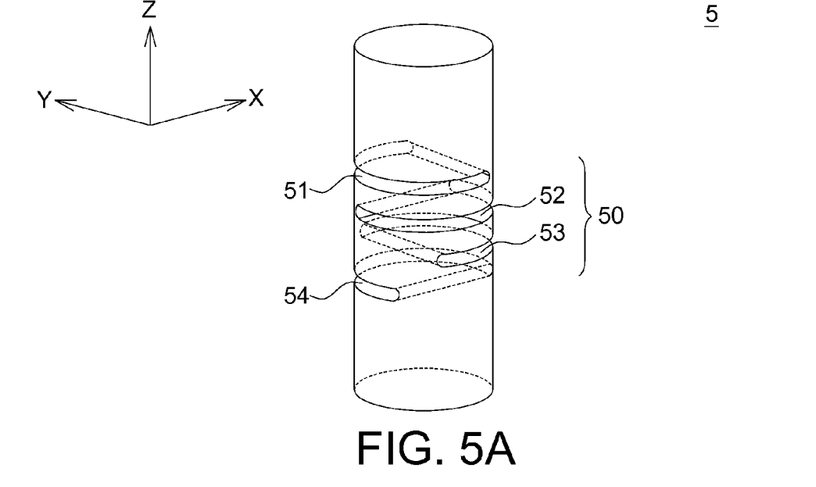
FIG. 5A illustrates a bionic fixing apparatus according to the fifth embodiment of the disclosure.

FIG. 5A illustrates a bionic fixing apparatus 5 according to the fifth embodiment of the disclosure. The bionic fixing apparatus 5 includes a flexible portion 50. The flexible portion 50 includes a first trench 51 and a second trench 52, a third trench 53 and a fourth trench 54 disposed on the surface of the flexible portion 50.

Figure 5B:
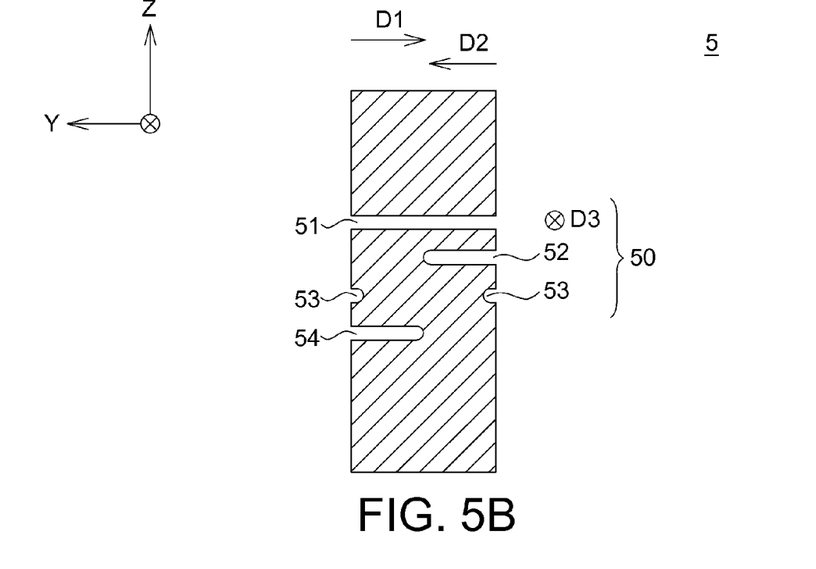
FIG. 5B illustrates a side view of the bionic fixing apparatus (in Y-Z plane) according to the fifth embodiment of the disclosure.

FIG. 5B illustrates a side view of the bionic fixing apparatus 5 (in Y-Z plane) according to the fifth embodiment of the disclosure. The first trench 51, the second trench 52, the third trench 53 and the fourth trench 54 are formed on the surface of the flexible portion 50 in sequence from top to bottom of the bionic fixing apparatus 5 as shown in FIGS. 5A and 5B. However, the disclosure is not limited thereto. The order of the first trench 51, the second trench 52, the third trench 53 and the fourth trench 54 formed on the surface of the flexible portion 50 may be different from that as shown in FIGS. 5A and 5B.

The difference between the bionic fixing apparatus 5 according to the fifth embodiment of the disclosure and the bionic fixing apparatus 4 according to the fourth embodiment of the disclosure is the order of the second trench 52 and the third trench 53 in the bionic fixing apparatus 5 and the order of the second trench 42 and the third trench 43 of the bionic fixing apparatus 4. As shown in FIG. 5B, the second trench 52 of the bionic fixing apparatus 5 according to the fifth embodiment of the disclosure is similar to the third trench 42 of the bionic fixing apparatus 4 according to the fourth embodiment of the disclosure, disposed along a second direction D2 in Y-Z plane, and extended on the surface of the flexible portion 50. The third trench 53 of the bionic fixing apparatus 5 according to the fifth embodiment of the disclosure is similar to the second trench 42 of the bionic fixing apparatus 4 according to the fourth embodiment of the disclosure, disposed along a third direction D3 in Y-Z plane, and extended on the surface of the flexible portion 50.

The following is an observation of the structure of the bionic fixing apparatus 5 from another point of view (another plane). In this embodiment, the second trench 52 of the bionic fixing apparatus 5 is disposed along track T3 in X-Y plane as shown in FIG. 1E, and extended on the surface of the flexible portion 50. That is, the second trench 52 is disposed along an arc line along radian $\pi$ to $2\pi$, and extended on the surface of the flexible portion 50. The third trench 53 of the bionic fixing apparatus 5 is disposed along track T4 in X-Y plane as shown in FIG. 1F, and extended on the surface of the flexible portion 50. That is, the third trench 53 is disposed along an arc line along radian $-\pi/2$ to $\pi/2$, and extended on the surface of the flexible portion 50. Other structures similar to those of the fourth embodiment are omitted here.

The first trench 51, the second trench 52, the third trench 53 and the fourth trench 54 according to the fifth embodiment of the disclosure are all arc lines with radian equal to $\pi$. However, the disclosure is not limited thereto.

In this embodiment, assumed that a 100 N external force parallel with Z-direction is applied to the bionic fixing apparatus 5, the bionic fixing apparatus 5 may generate a displacement of approximately $1.087 \times 10^{-1}$ mm. The displacement may be used as a buffer when the bionic fixing apparatus 5 is subjected to an external force, such that modulus of elasticity of the bionic fixing apparatus 5 may be decreased effectively.

In the first embodiment to the fifth embodiment mentioned above, a 100 N external force parallel with Z-direction is applied to the bionic fixing apparatus, and the displacement of the bionic fixing apparatus is measured. Similarly, a bionic fixing apparatus of a comparative example is proceeded a stress test, and compared with the bionic fixing apparatus of the first embodiment to the fifth embodiment. Here, the bionic fixing apparatus of the comparative example does not include any flexible portion. That is, the bionic fixing apparatus of the comparative example does not have any trench or pore on the surface.

A 100 N external force parallel with Z-direction is applied to the bionic fixing apparatus of the comparative example, and the bionic fixing apparatus of the comparative example may generate a displacement of approximately $9.023 \times 10^{-4}$ mm, which is much smaller than the displacement of the embodiments mentioned above. That is, the structure of the comparative example could not be a buffer when subjected to an external force, and the bionic fixing apparatus of the comparative example is easily loosened, or make the tissue of organisms sag, necrosis, wear.

Sixth Embodiment

Figure 6:
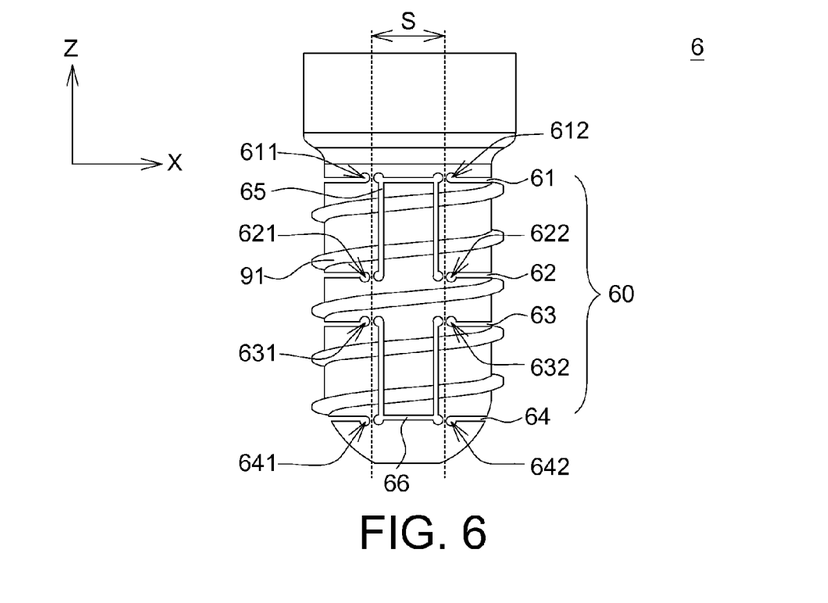
FIG. 6 illustrates a bionic fixing apparatus according to the sixth embodiment of the disclosure.

FIG. 6 illustrates a bionic fixing apparatus 6 according to the sixth embodiment of the disclosure. The bionic fixing apparatus 6 includes a flexible portion 60. The flexible portion 60 includes a first trench 61, a second trench 62, a third trench 63 and a fourth trench 64 disposed on the surface of the flexible portion 60. Every trench has a first end and a second end.

For example, the first trench 61 has a first end 611 and a second end 612; the second trench 62 has a first end 621 and a second end 622; the third trench 63 has a first end 631 and a second end 632; the fourth trench 64 has a first end 641 and a second end 642. An interval S is disposed between the first ends 611, 621, 631, 641 and the second ends 612, 622, 632, 642. That is, the first end 611 and the second end 612 disconnect to each other, the first end 621 and the second end 622 disconnect to each other, the first end 631 and the second end 632 disconnect to each other, and the first end 641 and the second end 642 disconnect to each other, such that the first trench 61, the second trench 62, the third trench 63 and the fourth trench 64 are not formed as enclosed regions.

The first trench 61, the second trench 62, the third trench 63 and the fourth trench 64 according to the sixth embodiment of the disclosure are similar to the trench 11 according to the first embodiment of the disclosure, and would not be narrated more herein. It should be noted that the first trench 61, the second trench 62, the third trench 63 and the fourth trench 64 are formed along an arc line with radian larger than π and smaller than 2π, and extended on the surface of the flexible portion 60 as shown in FIG. 6.

In this embodiment, the bionic fixing apparatus further includes a fifth trench 65 and a sixth trench 66 disposed on the surface of the flexible portion 60. The fifth trench 65 and the sixth trench 66 are U-shaped, and openings of the two U-shaped trenches are opposed to each other. As shown in FIG. 6, the fifth trench 65 and the sixth trench 66 are disposed in the interval S between the first ends 611, 621, 631, 641 and the second ends 612, 622, 632, 642. However, the fifth trench 65 and the sixth trench 66 are disconnected to the first trench 61, the second trench 62, the third trench 63 and the fourth trench 64.

In addition, the bionic fixing apparatus 6 according to the sixth embodiment of the disclosure may include a thread portion 91 surrounded on the surface of the bionic fixing apparatus 6, and the thread portion 91 and the flexible portion 60 are one-piece formed. After the bionic fixing apparatus 6 is implanted in an organism, the thread portion 91 may help the bionic fixing apparatus 6 to fix in the surrounding biological tissue.

Seventh Embodiment

Figure 7:
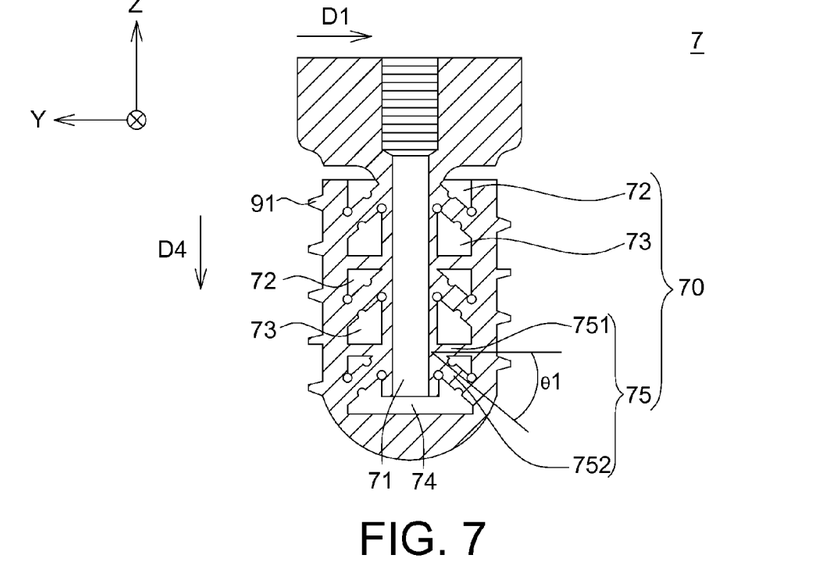
FIG. 7 illustrates a bionic fixing apparatus according to the seventh embodiment of the disclosure.

FIG. 7 illustrates a bionic fixing apparatus 7 according to the seventh embodiment of the disclosure. The bionic fixing apparatus 7 includes a flexible portion 70. The flexible portion 70 includes a trench 71 disposed along a fourth direction D4 in Y-X plane and extended on the surface of the flexible portion 70. In this embodiment, the fourth direction D4 is parallel with a force-receiving direction of the bionic fixing apparatus 7.

In the seventh embodiment, the bionic fixing apparatus 7 may further include a plurality of pores 72, 73, 74. In this embodiment, the pore 72 may be triangular, the pore 73 may be trapezoidal, and the pore 74 may be a shape combined with triangle (or trapezoid) and rectangle. These pores and the trench 71 may form a plurality of stress-bearing areas 75 on the surface of the flexible portion 70.

In the embodiment, the stress-bearing areas 75 include a first sub-area 751 and a second sub-area 752. The first sub-area 751 is disposed along a first direction D1 perpendicular to a force-receiving direction of the bionic fixing apparatus 7. An included angle between first sub-area 751 and the second sub-area 752 is a first angle θ1, and the first angle θ1 may range between 0 and 45 degrees. Since the bionic fixing apparatus 7 according to the seventh embodiment includes the trench 71 and the plurality of pores 72, 73, 74, the stress-bearing areas 75 are formed on the surface of the flexible portion 70, such that the bionic fixing apparatus 7 may spread the stress from outside and prevent stress concentration and stress shielding, and the modulus of elasticity of the bionic fixing apparatus 7 may be effectively decreased to prevent the bionic fixing apparatus 7 from loosening.

It should be noted that although the pore 72 is triangular, the pore 73 is trapezoidal, and the pore 74 is a shape combined with triangle (or trapezoid) and rectangle according to the seventh embodiment of the disclosure, the disclosure is not limited thereto. Instead, the shape of the pores may correspond to the trench 71 to form a plurality of stress-bearing areas 75, and the stress-bearing areas 75 should include a first sub-area 751 extended along the first direction D1 and a second sub-area 752, wherein an included angle between first sub-area 751 and the second sub-area 752 ranges between 0 and 45 degrees. If the included angle (first angle θ1) is larger than 45 degrees, then the modulus of elasticity of the bionic fixing apparatus 7 would significantly increase.

In addition, the bionic fixing apparatus 7 according to the seventh embodiment of the disclosure may also include a thread portion 91 surrounded on the surface of the bionic fixing apparatus 7, and the thread portion 91 and the flexible portion 70 are one-piece formed.

The complex micro-structure in the embodiments mentioned above may be manufactured by an additive manufacturing (AM) process. The trenches of the flexible portion, or the stress-bearing areas and the thread portion in some embodiments are all one-piece formed. Further, various shapes and arrangements according to the embodiments of the disclosure may be easily completed by the additive manufacturing process. On the contrary, the conventional process (including a special sintering process or a surface coating process to the implants, and then executing a surface treatment by laser to enhance bone integration) is not only more complex, but also needs more manufacturing cost, which is not suitable to manufacture the structures in the embodiments of the disclosure.

According to the embodiments of the disclosure, a material of the bionic fixing apparatus may include metals, alloys, ceramics or polymeric biomaterials. In some embodiments, the bionic fixing apparatus may be a hollow structure. The hollow structure may correspond to the trenches of the flexible portion to produce an atmosphere which is more suitable for cells or tissues of aquatic organisms growing.

It should be noted that a depth of the trench are not limited in the embodiments mentioned above. Then the bionic fixing apparatus is a hollow structure, the trench may be deep enough to reach the hollow portion of the bionic fixing apparatus. That is, the trench may be formed as a through hole penetrating from the surface of the flexible portion to the hollow portion. But the disclosure is not limited thereto. An interval may be formed between the trench and the hollow portion, such that the trench and the hollow portion are disconnected.

The bionic fixing apparatus according to the embodiments of the disclosure may be applied to fix different parts of the organism. For example, the bionic fixing apparatus may be applied to an artificial tooth root, vertebral screws, artificial discs, intramedullary nails or screws. Since the bionic fixing apparatus may be manufactured by the additive manufacturing process, it is easy to design different structures to correspond to different parts of the organism.

Compared with the fixing structure with high modulus of elasticity such as conventional bone nail, the bionic fixing apparatus according to the embodiments of the disclosure having the trench structure may effectively decrease modulus of elasticity of the implants to prevent the tissue of organisms from sagging, necrosis, wearing, or to prevent the implants from loosening.

In addition, the complex micro-structure in the embodiments mentioned above may be manufactured by an additive manufacturing process. The trenches of the flexible portion, or the stress-bearing areas and the thread portion in some embodiments are all one-piece formed. Further, various shapes and arrangements of the pores according to the embodiments of the disclosure may be easily completed by the additive manufacturing process. On the contrary, the conventional process (including a special sintering process or a surface coating process to the implants, and then executing a surface treatment by laser to enhance bone integration) is not only more complex, but also needs more manufacturing cost, which is not suitable to manufacture the structures in the embodiments of the disclosure.

The additive manufacturing process may also be known as rapid prototyping (RP), rapid manufacturing (RM) or 3D Printing. It is rectified as additive manufacturing process by American Society for Testing and Materials (ASTM) in 2009. Researchers have divided the additive manufacturing process into seven types as show in Table 1. The seven types include: Vat Photopolymerization, Material Jetting, Binder Jetting, Material Extrusion, Powder Bed Fusion, Sheet Lamination, and Directed Energy Deposition.

TABLE 1

| Process | Material | Application |
|---|---|---|
| Vat Photopolymerization | photopolymers | Prototyping |
| Material Jetting | polymers, waxes | Prototyping |
| Binder Jetting | polymers, metals | Casting Pattern |
| Material Extrusion | foundry sand | Prototyping, Casting Molds, Direct Part |
| Powder Bed Fusion | polymers | Prototyping |
| Sheet Lamination | polymers, metals | Prototyping, Direct Part |
| Directed Energy Deposition | paper, metals | Prototyping, Direct Part |

The characteristics of the additive manufacturing process are that the three-dimensional (3D) image is transferred to two-dimensional (2D) cross-sections, and products can be made layer by layer according to the two-dimensional cross-sections, to form a three-dimensional object. Compared with the conventional process, the additive manufacturing process may avoid wasting materials, and be more suitable for application of highly complicated structure, customized, and small or medium amount of production.

During the manufacturing process of the bionic fixing apparatus according to the embodiments of the disclosure, the 3D digital model of the bionic fixing apparatus is transferred to a 2D cross-section having thickness between 20-50 μm. And a feeding system will spread out a 20-50 μm thickness layer of powder materials (such as metals, alloys, ceramics or polymeric biomaterials) with particle size smaller than 25 μm in a low-oxygen atmosphere (concentration of $O_2$ is smaller than 10,000 ppm).

Then, the fiber laser beam (with wavelength 1070 nm) is focused to the laminated area (50-150 μm) by the scanning galvanometer. The focused beam is moved corresponding to the 2D cross-sections (the moving speed is 500-1500 mm/s), such that the powder materials is heating up above their melting point to adding a layer of structure. By repeating this procedure, the 3D bionic fixing apparatus can be made layer by layer according to the 2D cross-sections. The additive manufacturing process may produce the highly complicated shapes, inner flow channels, and inner structures which are difficult to make by the conventional process.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:
1. A bionic fixing apparatus, comprising:
   a flexible portion comprising a plurality of trenches, wherein each of the trenches has a first end and a second end, an interval is disposed between the first end and the second end, and the trenches are disposed for spreading the stress applied on the bionic fixing apparatus,
   wherein one of the trenches is a first arc line with radian 0 to $\pi$, and the first arc line is extended on a circular surface of the flexible portion and parallel to a first plane, and the first plane is perpendicular to a force-receiving direction of the bionic fixing apparatus, and
   wherein another one of the trenches is a second arc line with radian $\pi/2$ to $3\pi/2$, and the second arc line is extended on the circular surface of the flexible portion and parallel to a second plane different from the first plane, and the second plane is perpendicular to the force-receiving direction.

2. The bionic fixing apparatus according to claim 1, further comprising at least one second trench disposed within the interval between the first end and second end and the at least one second trench is extended on the circular surface of the flexible portion along a third direction in the second plane, the third direction is parallel to the force-receiving direction of the bionic fixing apparatus, the first direction and the second direction.

3. The bionic fixing apparatus according to claim 1, further comprising a plurality of second trenches, disposed within the interval between the first end and the second end, wherein at least one of the second trenches disposed on the circular surface of the flexible portion is U-shaped.

4. The bionic fixing apparatus according to claim 1, wherein a material of the bionic fixing apparatus comprises metals, alloys, ceramics or polymeric biomaterials.

5. The bionic fixing apparatus according to claim 1, further comprising:
   a thread portion surrounded on the circular surface of flexible portion, wherein the thread portion and the flexible portion are one-piece formed.

6. The bionic fixing apparatus according to claim 1, wherein the bionic fixing apparatus is a hollow structure.

7. The bionic fixing apparatus according to claim 1, wherein the bionic fixing apparatus is applied to an artificial tooth root, vertebral screws, artificial discs, intramedullary nails or bone screws.

8. A bionic fixing apparatus, comprising:
   a flexible portion comprising a plurality of trenches, wherein each of the trenches has a first end and a second end, an interval is disposed between the first end and the second end, and the trenches are disposed for spreading the stress applied on the bionic fixing apparatus,
   wherein one of the trenches is a first arc line with radian $\pi/2$ to $3\pi/2$, and the first arc line is extended on a circular surface of the flexible portion and parallel to a first plane, and the first plane is perpendicular to a force-receiving direction of the bionic fixing apparatus, and
   wherein another one of the trenches is a second arc line with radian $\pi$ to $2\pi$, and the second arc line is extended on the circular surface of the flexible portion and parallel to a second plane different from the first plane, and the second plane is perpendicular to the force-receiving direction.

9. A bionic fixing apparatus, comprising:
   a flexible portion comprising a plurality of trenches, wherein each of the trenches has a first end and a second end, an interval is disposed between the first end and the second end, and the trenches are disposed for spreading the stress applied on the bionic fixing apparatus, wherein one of the trenches is a first arc line with radian $\pi$ to $2\pi$, and the first arc line is extended on a circular surface of the flexible portion and parallel to a first plane, and the first plane is perpendicular to a force-receiving direction of the bionic fixing apparatus, and wherein another one of the trenches is a second arc line with radian $-\pi/2$ to $\pi/2$, and the second arc line is extended on the circular surface of the flexible portion and parallel to a second plane different from the first plane, and the second plane is perpendicular to the force-receiving direction.

10. A bionic fixing apparatus, comprising:

a flexible portion comprising a plurality of trenches, wherein each of the trenches has a first end and a second end, an interval is disposed between the first end and the second end, and the trenches are disposed for spreading the stress applied on the bionic fixing apparatus, wherein one of the trenches is a first arc line with radian $-\pi/2$ to $\pi/2$, and the first arc line is extended on a circular surface of the flexible portion and parallel to a first plane, and the first plane is perpendicular to a force-receiving direction of the bionic fixing apparatus, and wherein another one of the trenches is a second arc line with radian 0 to $\pi$, and the second arc line is extended on the circular surface of the flexible portion and parallel to a second plane different from the first plane, and the second plane is perpendicular to the force-receiving direction.

11. A bionic fixing apparatus, comprising:

a flexible portion comprising a plurality of trenches, wherein each of the trenches has a first end and a second end, an interval is disposed between the first end and the second end, and the trenches are disposed for spreading the stress applied on the bionic fixing apparatus, wherein one of the trenches is extended on a surface of the flexible portion and parallel to a first plane, and the first plane is perpendicular to a force-receiving direction of the bionic fixing apparatus, and wherein another one of the trenches is extended on the surface of the flexible portion and parallel to a second plane, and the second plane is perpendicular to the first plane.

12. The bionic fixing apparatus according to claim 11, further comprising a plurality of pores, wherein the pores and the trench form a plurality of stress-bearing areas on the surface of the flexible portion.

13. The bionic fixing apparatus according to claim 12, wherein the stress-bearing areas comprise a first sub-area and a second sub-area, the first sub-area is disposed along the first direction, an included angle between first sub-area and the second sub-area is a first angle, and the first angle ranges between 0 and 45 degrees.

* * * * *